United States Patent

Mahieu et al.

Patent Number: 5,833,997

Date of Patent: *Nov. 10, 1998

[54] FLUORINATED HYDROCARBON COMPOUNDS, THEIR USE IN COSMETIC COMPOSITIONS, METHOD OF PREPARING THEM AND COSMETIC COMPOSITIONS CONTAINING THEM

[75] Inventors: Claude Mahieu, Paris; Eric Bollens, Saint-Maurice; Myriam Mellul, L'Hay-les-Roses, all of France

[73] Assignee: L'Oreal, Paris, France

[*] Notice: The term of this patent shall not extend beyond the expiration date of Pat. No. 5,705,165.

[21] Appl. No.: 457,131

[22] Filed: Jun. 1, 1995

Related U.S. Application Data

[63] Continuation of Ser. No. 94,196, filed as PCT/FR92/01140, Dec. 3, 1992, abandoned.

[30] Foreign Application Priority Data

Dec. 4, 1991 [FR] France .................. 91 15019

[51] Int. Cl.$^6$ .................. A61K 7/00; A61K 7/07
[52] U.S. Cl. .................. 424/401; 424/70.1; 424/62; 514/759
[58] Field of Search .................. 424/401, 78.03, 424/70.11, 70.1, 62; 514/759

[56] References Cited

U.S. PATENT DOCUMENTS

| | | |
|---|---|---|
| 4,126,702 | 11/1978 | Vanlerberghe et al. . |
| 4,765,975 | 8/1988 | Iovanni et al. . |
| 4,859,797 | 8/1989 | Lampin et al. . |
| 4,880,620 | 11/1989 | Vanlerberghe et al. . |
| 4,895,952 | 1/1990 | Marty et al. . |

FOREIGN PATENT DOCUMENTS

| | | |
|---|---|---|
| 2416222 | 8/1979 | France . |
| 2516920 | 5/1983 | France . |
| 2052579 | 5/1972 | Germany . |

OTHER PUBLICATIONS

Matsuo et al, "Cosmetic skin and hair preparations containing fluoroalkyl-containing ethers.", Chemical Abstracts, vol. 110, No. 16, Apr. 1989, Abstract No. 141248p, p. 386, col. 2.

*Primary Examiner*—Sally Gardner-Lane
*Attorney, Agent, or Firm*—Pillsbury Madison & Sutro

[57] ABSTRACT

Fluorinated hydrocarbon compounds have formula (I):

$$R_F-(CH_2)_n-X-[C_3H_5(OH)]-(Y)_x-R_H,$$

in which $C_3H_5(OH)$ represents structures (Ia) or (Ib):

$$-CH_2-CH(OH)-CH_2- \quad \text{or} \quad (Ia)$$

$$-CH(CH_2OH)-CH_2- \quad (Ib)$$

$R_F$ is a perfluorinated $C_4-C_{20}$ alkyl radical or a mixture of perfluorinated $C_4-C_{20}$ radicals; $R_H$ is a straight or branched $C_1-C_{22}$ alkyl radical or a mixture of straight or branched $C_1-C_{22}$ alkyl radicals or an aryl or aralkyl radical; n is from 0 to 4; X stands for O, S, (a) S=O or (b) O=S=O ;

x stands for 0 or 1; Y stands for O, S, (a) or (b); with the proviso that when X=S, (a) or (b), Y is not S, (a) or (b). The use of said compounds as amphiphilic compounds, the method of preparing them, and the cosmetic compositions containing them are also disclosed.

2 Claims, No Drawings

FLUORINATED HYDROCARBON COMPOUNDS, THEIR USE IN COSMETIC COMPOSITIONS, METHOD OF PREPARING THEM AND COSMETIC COMPOSITIONS CONTAINING THEM

This is a continuation of application Ser. No. 08/094,196, filed as PCT/FR92/01140, Dec. 3, 1992 now abandoned.

The present invention relates to hydro- and fluorocarbon compounds which are useful, in particular, in cosmetic compositions, and to a process for preparing them, as well as to cosmetic compositions containing these compounds.

It is known to use perfluoropolyethers, in particular in processes for cleansing, protecting and making-up the skin, or alternatively for washing the hair. These compounds are known for their low surface tension and their ease of spreading, but possess very low solubility in most fluids other than fluorinated fluids, which makes it very difficult to formulate them in cosmetic compositions. Some of these compounds, perfluoro(methyl isopropyl ethers), are known by the name of "FOMBLIN HC", marketed by the company MONTEFLUO.

The Applicant has now discovered new compounds which, in contrast to the known FOMBLINs, possess good solubility, in particular in the standard solvents used in cosmetics, such as lower alcohols as well as fats and conventional oils. Their amphiphilic character, their properties and their compatibility with solvents make it possible, in particular, to prepare homogeneous and stable compositions and, for example, to ensure good stability of the emulsions in which they participate.

Thus, the present invention relates to the compounds of formula:

$$R_F\text{—}(CH_2)_n\text{—}X\text{—}[C_3H_5(OH)]\text{—}(Y)_x\text{—}R_H \quad (I)$$

in which $C_3H_5(OH)$ represents the structures:

—CH$_2$—CH—CH$_2$—     (Ia)
        |
        OH

—CH—CH$_2$—     (Ib)
 |
CH$_2$OH $R_F$ represents a perfluorinated $C_4$–$C_{20}$ alkyl radical or a mixture of perfluorinated $C_4$–$C_{20}$ alkyl radicals;

$R_H$ represents a linear or branched $C_1$–$C_{22}$ alkyl radical or a mixture of linear or branched $C_1$–$C_{22}$ alkyl radicals or an aryl or aralkyl radical;

n is between 0 and 4;

n is between 0 and 4; X represents O, S, S or S(=O)$_2$ ;

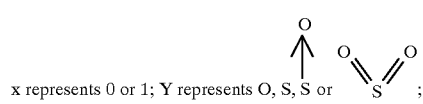
x represents 0 or 1; Y represents O, S, S or S(=O)$_2$ ;

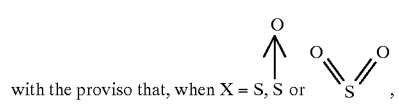
with the proviso that, when X = S, S or S(=O)$_2$,

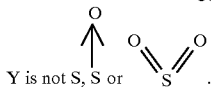
Y is not S, S or S(=O)$_2$.

Among these compounds, preferred compounds are those for which $R_F$ denotes a perfluorinated $C_6$–$C_{12}$ alkyl radical, $R_H$ denotes a linear or branched $C_3$–$C_{18}$ alkyl radical, a $C_6$–$C_{10}$ aryl radical or a $C_7$–$C_{15}$ aralkyl radical and n is 2. Preferably, X is O or S and Y is O.

Among linear or branched alkyl radicals, butyl, octyl, 2-ethylhexyl, decyl, dodecyl, tetradecyl, hexadecyl, 2-hexyldecyl, stearyl and isostearyl radicals may be mentioned in particular.

Among aralkyl radicals, 4-nonylphenyl and benzyl radicals may be mentioned in particular, and among aryl radicals, the phenyl radical.

The compounds of formula (I) according to the invention may be prepared by carrying out the reaction of a fluorinated compound containing acidic hydrogen, of formula (II):

$$R_F\text{—}(CH_2)_n\text{—}X\text{—}H \quad (II)$$

with an epoxide of formula (III):

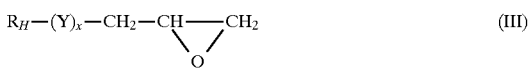

or the reaction of a hydrocarbon compound containing acidic hydrogen, of formula (IV):

$$R_H\text{—}(Y)_x\text{—}H \quad (IV)$$

with a fluorinated epoxide of formula (V):

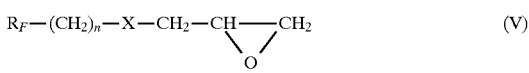

in the presence of a basic or acidic compound playing the part of reactant or catalyst, to obtain the corresponding compound of formula (I), the substituents $R_F$, $R_H$, n and x in the formulae (II) and (III), (IV) and (V) having the same meaning as in the formula (I) and X denoting O or S, Y denoting O or S, with the proviso that, when X is S, Y is not S, and by oxidizing, where appropriate, the mercaptan function to sulfoxide or sulfone with hydrogen peroxide.

The compounds of formula (V) are described, in particular, in U.S. Pat. No. 3,976,698 or in Patent Applications EP 300,358 and DE 2,018,461.

When X represents S in the formula (II) or (IV), it is preferable to use a basic compound.

The compounds playing the part of a reactant or catalyst can hence be basic, such as alkali metals, alkali metal or alkaline earth metal hydroxides, alkali metal alcoholates such as the methylates or tert-butylates, alkali metal hydrides such as sodium hydride, and tertiary amines such as pyridine or triethylamine. They can also be Lewis bases, among which cesium, rubidium and potassium fluorides may be mentioned. These compounds may also be supported on a solid such as alumina. Preferably, an alkali metal alcoholate such as sodium methylate or a tertiary amine such as pyridine is used.

These compounds can also be acidic, in particular when the starting material of formula (II) or (IV) is an alcohol. Such acids can be inorganic acids or their salts with tertiary amines, or alternatively so-called Lewis acids such as boron trifluoride, tin tetrachloride and antimony pentachloride, used alone, in solution or combined with a conventional support.

The concentration of the acidic or basic compounds playing the part of a reactant or catalyst and employed in the reaction of preparation of the compounds of formula (I) can be between 1 and 100 mol %, and preferably between 2 and 10 mol %, relative to the fluorinated compound containing acidic hydrogen of formula (II) or (IV).

The preparation reaction may be carried out in the presence of a solvent or in the absence of a solvent.

As a solvent, it is possible to use aliphatic hydrocarbons such as heptane and hexane or cyclic hydrocarbons such as cyclohexane, aromatic hydrocarbons such as toluene, ethers such as ethyl or isopropyl ether, cyclic ethers such as dioxane, or alternatively acetonitrile, dimethylformamide, N-methylpyrrolidone or dimethylacetamide.

When the compound of formula (II) or (IV) is a thiol (X=S), alcohols such as methanol, ethanol or isopropanol may also be used as a solvent.

To prepare the compounds according to the invention, the compound containing acidic hydrogen of formula (II) or (IV) may first be mixed under an inert atmosphere with the acidic or basic reactant or catalyst. To carry out the mixing, it is possible to work at a temperature of between 20° and 180° C., and preferably between 50° and 150° C. Inert atmosphere is understood to mean, for example, a nitrogen, argon or helium atmosphere.

The mixing may be performed, depending on the nature of the compound containing acidic hydrogen and the reactant or catalyst, in the absence or in the presence of a solvent.

The epoxide of formula (III) or (V) is added to the mixture obtained, it being possible for this addition to be performed in a single operation, or gradually over a period which can range from 30 minutes to 2 hours, for example.

The reaction time is then between approximately 1 hour and 24 hours, and preferably between 1 hour and 3 hours.

The compound arising from the reaction may be oxidized when the latter contains a mercaptan function, to sulfoxide or to sulfone, in the presence of hydrogen peroxide in an acid medium, according to methods which are known, in particular in French Patent Applications FR 2,099,092 and FR 2,516,920.

It may, in addition, be necessary to neutralize the mixture obtained, and the compound synthesized may be separated in a conventional manner, by distillation for example.

When the reaction of preparation of the compounds of formula (I) is performed in the presence of a basic compound, it yields only compounds for which $C_3H_5(OH)$ represents the group (Ia). In the case where the reaction is performed in the presence of an acidic compound, a mixture of two compounds corresponding to the meanings (Ia) and (Ib) of $C_3H_5(OH)$ may be obtained.

The compounds according to the invention can take the form of an oil or a solid at room temperature.

Another subject of the invention relates to the use of products of formula (I), amphiphilic compounds, in particular in cosmetic compositions.

Generally speaking, these compounds used in cosmetic compositions enable the cosmetic properties thereof to be improved. They impart softness, sheen and a non-sticky feel to keratinous materials such as skin, hair and nails. Moreover, some of these compounds take the form of a colorless oil; they can enable transparent emulsions to be obtained.

Thus, the present invention also relates to cosmetic compositions which are characterized in that they contain at least one compound of formula (I) defined above.

These compositions can take the form of emulsions, of milks or of creams, of oily or oleoalcoholic lotions, or the form of fatty or oleoalcoholic gels, of vesicular dispersions based on ionic or nonionic amphiphilic lipids, of solid sticks, of paste, of spray or of aerosol foam.

Depending on the form of the compositions in which the compounds of the invention are incorporated, these compositions contain, moreover, the conventional adjuvants and additives for the chosen form.

More specifically, these compositions can be milks and creams for skin or hair care, make-up removal creams, lotions or milks, antisun creams, gels, milks or lotions, shaving creams or foams, aftershave lotions, shampoos or after-shampoo products, body deodorants, toothpastes, lacquers or lip or nail care products.

These cosmetic compositions may also be used as a make-up product for the eyelashes, eyebrows, nails, lips or skin, as creams- for treating the epidermis, make-up foundations, lipsticks, eyeshadows or blushers, eyeliners or mascara, or nail varnishes, for example.

According to the invention, the compounds of formula (I) represent from 0.1 to 25%, and preferably from 0.1 to 15%, of the total weight of the composition.

Among conventional adjuvants for this type of composition, there may be present, in addition, in the compositions according to the invention, fats of a conventional nature, organic solvents, silicones, thickeners, demulcents, UV-A or UV-B or broad-band sunscreen agents, antifoams, hydrating agents, humectants, fragrances, preservatives, surfactants, fillers, sequestering agents, emulsifiers, anionic, cationic, nonionic or amphoteric polymers or mixtures thereof, antiperspirants, alkalinizing agents, colorants, pigments, propellants, antioxidants and anti-free-radical agents.

More specifically, as fats, it is possible to use an oil or wax or mixture thereof, fatty acids, fatty alcohols, fatty acid esters such as $C_6$ to $C_{18}$ fatty acid triglycerides, petrolatum, paraffin, lanolin and hydrogenated or acetylated lanolin.

Among oils, mineral, animal, vegetable or synthetic oils may be mentioned, and in particular liquid petrolatum and paraffin, castor, jojoba and sesame oils, as well as silicone oils and gums and isoparaffins.

Among animal, fossil, vegetable, mineral or synthetic waxes, beeswax, carob and candelilla waxes, ozokerites and microcrystalline waxes may be mentioned, as well as silicone waxes and resins.

Among the organic solvents commonly used in cosmetic compositions, there may be mentioned, more specifically, $C_1$ to $C_6$ lower polyhydric alcohols and monohydric alcohols such as ethanol, isopropanol, propylene glycol, glycerol and sorbitol, ketones such as acetone, esters such as butyl acetate or ethyl acetate, and toluene, for example.

As a thickening agent, cellulose derivatives, polyacrylic acid derivatives, guar or carob gums, as well as xanthan gum, may be mentioned, for example.

Among surfactants, nonionic surfactants such as ($C_8$–$C_{24}$ alkyl)polyglycosides in which the number of glucoside unit is between 1 and 15, and nonionic surfactants of the polyglycerolated type, may be mentioned in particular.

The alkylpolyglycosides are, in particular, the products sold under the name APG, such as the products APG 300®, APG 350®, APG 500®, APG 550®, APG 625®; and the products sold by the company Seppic under the names TRITON CG 110® and TRITON CG 312®.

The polyglycerolated compounds are derivatives resulting from the condensation of 1 to 10, and preferably 2 to 6, mol of glycidol per mole of $C_{10}$–$C_{14}$ alcohol or alpha-diol or of $C_{12}$–$C_{18}$ fatty acid diglycolamide, as are described in Patents FR 1,477,048, 2,328,763, 2,091,516 and 2,169,787.

The vesicular dispersions of ionic or nonionic amphiphilic lipids mentioned above may be prepared according to conventional processes, a non-limiting list of which is to be found in "Les liposomes en biologie cellulaire et pharmacologie" [Liposomes in cell biology and pharmacology] Edition INSERM/John Libbery Eurotext, (1987), p. 6 to 18.

For the compositions in the form of toothpaste, it is possible to use conventional adjuvants and additives such as polishing agents, for instance silica, active agents such as fluorides, for instance sodium fluoride, and, where appropriate, sweetening agents such as sodium saccharinate.

The examples which follow are intended to illustrate the invention and could not be considered to limit its scope.

PREPARATION EXAMPLES

Example 1

1-(2'-F-hexylethylthio)-3-(2"-ethylhexyloxyl-2-propanol a) in the presence of sodium methylate 3.6 g of a methanolic solution of sodium methylate (approximately 30%—5.54 meq $g^{-1}$) are added in the course of one minute at a temperature of 25° C., with stirring and under a stream of nitrogen, to 152 g of 2-F-hexylethanethiol.

The mixture is heated to 70° C. The methanol present in the medium is evaporated off under vacuum.

2-Ethylhexyl glycidyl ether (74.4 g) is then added dropwise in the course of one hour. The temperature of the mixture is maintained at between 60° and 70° C. during the addition of the epoxide.

When the addition is complete, the temperature is brought to 25° C.

The mixture is neutralized using 20 ml of normal HCl.

The 1-(2'-F-hexylethylthio)-3-(2"-ethylhexyloxy)-2-propanol is separated by distillation: b.p.=141° C./66.5 Pa.

175 g (77%) of a colorless translucent oil are obtained.

| Elemental analysis: | | | | |
|---|---|---|---|---|
| | % C | % H | % S | % F |
| Calculated | 40.28 | 4.80 | 5.66 | 43.60 |
| Measured | 40.37 | 4.82 | 5.55 | 43.74 | b) in the presence of potassium fluoride deposited on alumina 304 g of 2-F-hexylethanethiol are introduced into a 1-liter reactor. 7.6 g of potassium fluoride deposited on alumina ($5.5 \times 10^{-3}$ mol of $F^-$/g) are added under a stream of nitrogen. While the temperature is maintained at 40° C., 148.8 g of 2-ethylhexyl glycidyl ether are added in the course of 2 hours. The mixture is left stirring at 25° C. for 4 hours.

500 ml of dichloromethane are then added to the reaction mixture.

The potassium fluoride deposited on alumina is then removed by filtration through No. 4 sintered glass. After evaporation of the dichloromethane, the 1-(2'-F-hexylethylthio)-3-(2"-ethylhexyloxy)-2-propanol is separated by distillation under reduced pressure (148°–150° C./6.65 Pa).

340 g (75%) of a colorless oil are obtained.

| Elemental analysis: | | | | |
|---|---|---|---|---|
| | % C | % H | % S | % F |
| Calculated | 40.28 | 4.80 | 5.66 | 43.60 |
| Measured | 39.94 | 4.75 | 5.38 | 43.76 |

Example 2

1-(2'-F-octylethylthiol-3-(2"-ethylhexyloxyl-2-propanol

The compound is prepared in a manner similar to the preparation described in Example 1, wherein the following are used:

288 g of 2-F-octylethanethiol 5.4 g of a methanolic solution of sodium methylate (5.54 meq $g^{-1}$)

111.6 g of 2-ethylhexyl glycidyl ether 30 ml of normal HCl 337 g (81%) of a colorless translucent oil are obtained.

| Elemental analysis: | | | | |
|---|---|---|---|---|
| | % C | % H | % S | % F |
| Calculated | 37.84 | 4.08 | 4.81 | 48.46 |
| Measured | 37.83 | 4.06 | 4.20 | 47.45 |

Example 3

1-(2'-F-octylethylthio)-3-butyloxy-2-propanol

According to the procedure described in Example 1, 40 g (0.31 mol) of butyl glycidyl ether are condensed in the course of 1 hour with 147.7 g (0.31 mol) of 2-F-octylethanethiol in the presence of 2.75 g of methanolic solution of sodium methylate (5.54 meq $g^{-1}$). When the reaction is complete, the mixture is neutralized with 15.5 ml of normal HCl.

After distillation (138°–142° C./6.65 Pa), 153 g of 1-(2'-F-octylethylthio)-3-butyloxy-2-propanol are obtained in the form of colorless oil.

Yield=80%.

| Elemental analysis: | | | | |
|---|---|---|---|---|
| | % C | % H | % S | % F |
| Calculated | 33.45 | 3.14 | 5.25 | 52.92 |
| Measured | 33.52 | 3,23 | 5.14 | 52.67 |

Example 4

1-(2'-F-octylethylthio)-3-phenoxy-2-propanol 2.65 g of a methanolic solution of sodium methylate (5.65 meq $g^{-1}$) are added at a temperature of 25° C., with stirring and under a stream of nitrogen, to 144 g (0.3 mol) of 2-F-octylethanethiol dissolved in 250 ml of diisopropyl ether.

The mixture is heated to 60° C. 45 g (0.3 mol) of phenyl glycidyl ether are added dropwise in the course of 45 minutes while the temperature is maintained at between 55 and 65° C.

When the reaction is complete, the mixture is neutralized with 15 ml of normal HCl.

After evaporation of the solvent, a pale yellow pasty product is obtained.

The 1-(2'-F-octylethylthio)-3-phenoxy-2-propanol is purified by distillation (166°–168° C./13.3 Pa).

115 g of a white solid are obtained.

Yield: 65%

Melting point: 64° C.

| Elemental analysis: | | | | |
|---|---|---|---|---|
| | % C | % H | % S | % F |
| Calculated | 36.20 | 2.40 | 5.09 | 51.24 |
| Measured | 36.20 | 2.38 | 4.94 | 51.19 |

Example 5

1-(2'-F-hexylethylthio)-3-dodecyloxy-2-propanol

According to the procedure described in Example 1, 121 g (0.5 mol) of dodecyl glycidyl ether are condensed in the course of 1 hour 30 minutes with 190 g (0.5 mol) of 2-F-hexylethanethiol in the presence of 4.42 g of methanolic solution of sodium methylate (5.65 meq g$^{-1}$).

When the reaction is complete, the mixture is neutralized with 25 ml of normal HCl.

The product is purified by molecular distillation in two runs.

1st run

Oil temperature=80°–90° C. under a vacuum of 0.13 Pa. 180 g of crude product are obtained.

2nd run

Oil temperature=130° C. under a vacuum of 0.13 Pa; the expected product distills.

157 g of a perfectly colorless oil are obtained, which oil is 1-(2'-F-hexylethylthio)-3-dodecyloxy-2-propanol.

Yield=50%.

| Elemental analysis: | | | | |
|---|---|---|---|---|
| | % C | % H | % S | % F |
| Calculated | 44.37 | 5.67 | 5.15 | 39.67 |
| Measured | 44.34 | 5.63 | 4.92 | 39.83 |

Example 6

1-(2'-F-hexylethylthio)-2-decanol

According to the procedure described in Example 1, 78 g (0.5 mol) of 1,2-epoxydecane are condensed in the course of 1 hour 30 minutes with 130 g (0.5 mol) of 2-F-hexylethanethiol in the presence of 4.4 g of methanolic solution of sodium methylate (5.65 meq g$^{-1}$).

When the reaction is complete, the mixture is neutralized with 25 ml of normal HCl.

After distillation (165°–170° C./66.5 Pa), 216 g of a white amorphous solid are obtained, which solid is 1-(2'-F-hexylethylthio)-2-decanol.

Yield=81%.

Melting point=47° C.

| Elemental analysis: | | | | |
|---|---|---|---|---|
| | % C | % H | % S | % F |
| Calculated | 40.30 | 4.70 | 5.98 | 46.04 |
| Measured | 40.06 | 4.62 | 6.13 | 45.63 |

Example 7

1-(2'-F-hexylethylthio)-2-hexanol

According to the procedure described in Example 1, 50 g (0.5 mol) of 1,2-epoxyhexane are condensed in the course of 1 hour 30 minutes with 190 g (0.5 mol) of 2-F-hexylethanethiol in the presence of 4.4 g of methanolic solution of sodium methylate (5.65 meq g$^{-1}$).

When the reaction is complete, the mixture is neutralized with 25 ml of normal HCl.

After distillation (128° C./133 Pa), 171 g of 1-(2'-F-hexylethylthio)-2-hexanol are obtained in the form of perfectly colorless oil.

Yield=71%.

| Elemental analysis: | | | | |
|---|---|---|---|---|
| | % C | % H | % S | % F |
| Calculated | 35.01 | 3.57 | 6.68 | 51.42 |
| Measured | 34.77 | 3.49 | 6.72 | 51.92 |

Example 8

1-(2'-F-octylethylthio)-2-hexanol

According to the procedure described in Example 1, 30 g (0.3 mol) of 1,2-epoxyhexane are condensed in the course of 1 hour with 144 g (0.3 mol) of 2-F-octylethanethiol in the presence of 2.7 g of methanolic solution of sodium methylate (5.65 meq g$^{-1}$).

When the reaction is complete, the mixture is neutralized with 15 ml of normal HCl.

After distillation (154° C./133 Pa), 115 g of an amorphous white solid are obtained, which solid is 1-(2'-F-octylethylthio)-2-hexanol.

Yield=67%.

Melting point=45° C.

| Elemental analysis: | | | | |
|---|---|---|---|---|
| | % C | % H | % S | % F |
| Calculated | 33.11 | 2.95 | 5.53 | 55.65 |
| Measured | 33.26 | 2.93 | 5.30 | 55.60 |

Example 9

1-(2'-F-hexylethyloxy)-3-(2"-ethylhexyloxy)-2-propanol 546 g (1.5 mol) of 2-F-hexylethanol are introduced into a 1-liter reactor.

5.61 g of potassium tert-butylate are added at 25° C. and under a nitrogen atmosphere. The mixture is stirred at 25° C. for 30 minutes to solubilize the tert-butylate in the 2-F-hexylethanol.

The mixture is brought to 150° C., and 93 g (0.5 mol) of 2-ethylhexyl glycidyl ether are added in the course of 75 minutes.

After 24 hours of reaction at 150° C., 5.61 g of potassium tert-butylate are added. This operation is repeated twice at 24-hour time intervals.

The excess 2-F-hexylethanol is then evaporated off, and 68 g (20%) of 1-(2'-F-hexylethoxy)-3-(2"-ethylhexyloxy)-2-propanol are obtained on distillation.

Boiling point=145° C. at 13.3 Pa.

Elemental analysis:

|  | % C | % H | % F |
|---|---|---|---|
| Calculated | 41.46 | 4.94 | 44.87 |
| Measured | 41.55 | 4.99 | 45.01 |

Example 10

Mixture of 1-(2'-F-hexylethoxy)-3-(2"-ethylhexyloxy)-2-propanol and 2-(2'-F-hexylethoxy)-3-(2"-ethylhexyloxy)-1-propanol (70:30 mixture)

1640 g (4.5 mol) of 2-F-hexylethanol are introduced into a 2-liter reactor. 4.4 ml of boron trifluoride etherate are added under a nitrogen atmosphere and at 25° C.

The mixture is brought to 80° C., and 111.6 g (0.6 mol) of 2'-ethylhexyl glycidyl ether are added dropwise in the course of 1 hour while the temperature is maintained at between 79° and 82° C. When the addition is complete, the mixture is heated for 90 minutes to 80° C.±2° C. After it has returned to room temperature, the mixture is washed twice with 300 ml of water which has been subjected to osmosis and then with 300 ml of water of pH=8 (NaOH). After settling has taken place, the organic phase is separated and distilled. The 2-F-hexylethanol is removed initially (40°–42° C./6.65 Pa), and the mixed product is then obtained in a 70% yield (230 g) in the form of a mixture of isomers whose relative proportion is determined by $^{13}$C NMR.

1-(2'-F-hexylethoxy)-3-(2"-ethylhexyloxy)-2-propanol: 70%

2-(2'-F-hexylethoxy)-3-(2"-ethylhexyloxy)-1-propanol: 30%.

Elemental analysis:

|  | % C | % H | % F |
|---|---|---|---|
| Calculated | 41.46 | 4.94 | 44.87 |
| Measured | 41.64 | 4.98 | 44.71 |

Example 11

1-(2'-F-hexylethylthio)-3-(2"-hexyldecyloxy)-2-propanol 63.4 g (0.17 mol) of 2-F-hexylethanethiol and then 0.35 g of pyridine are introduced at 25° C. into a 250-ml reactor placed under a stream of nitrogen. The mixture is heated gradually to reach 70° C. in the course of 40 minutes.

49.7 g (0.17 mol) of 2-hexyldecyl glycidyl ether are added in the course of 25 minutes while the temperature is maintained at 70° C.

When the addition is complete, the temperature is maintained for 18 hours at 70° C. After it has returned to 25° C., the product is treated for 200 ml of water, pH 5 (by adding HCl). After settling has taken place, followed by separation and two successive washes of the recovered organic phase with 200 ml of distilled water each time, the most volatile constituents of the product are removed by distillation under vacuum (oil 220° C.—vacuum 1.33 Pa).

The product is then purified by molecular distillation (oil 190° C.—vacuum 0.13 Pa). 74 g (66%) of an amber-colored oil are thereby obtained.

Elemental analysis:

|  | % C | % H | % S | % F |
|---|---|---|---|---|
| Calculated | 47.70 | 6.39 | 4.72 | 36.39 |
| Measured | 47.07 | 6.33 | 4.66 | 36.08 |

Example 12

1-(2'-F-octylethyloxy)-3-(octylthio)-2-propanol

According to the procedure described in Example 1, 130.5 g (0.25 mol) of 2-F-octylethyl glycidyl ether are condensed in the course of 75 minutes with 36.5 g (0.25 mol) of octanethiol in the presence of 2.21 g of methanolic solution of sodium methylate (5.65 meq g. When the reaction is complete, the mixture is neutralized with 12.5 ml of normal HCl.

After distillation (172° C./266 Pa), 76 g of 1-(2'-F-octylethyloxy)-3-(octylthio)-2-propanol are obtained, which product takes the form, at atmospheric pressure, of a white solid of melting point equal to 30° C. The $^{13}$C NMR and mass spectra are in agreement with the expected structure.

Elemental analysis:

|  | % C | % H | % S | % F |
|---|---|---|---|---|
| Calculated | 37.84 | 4.08 | 4.81 | 48.46 |
| Measured | 37.95 | 4.08 | 4.72 | 48.40 |

Example 13

1-(2'F-hexylethanesulfoxy)-3-(2"-ethylhexyloxy)-2-propanol 8.5 ml of 30% hydrogen peroxide are mixed with 0.1 ml of acetic acid in a 100-ml reactor. 28.3 g (0.05 mol) of 1-(2'-F-hexylethanethio)-3-(2"-ethylhexyloxy)-2-propanol, prepared in Example 1, are added at 25° C. The temperature rises to 42° C. After six hours of reaction, 50 ml of dichloromethane are added and the organic phase is recovered by separation after settling has taken place.

After three washes of the organic phase with 20 ml of distilled water, the solution is filtered and the solvent is then evaporated off under reduced pressure.

23 g (80%) of a colorless viscous oil are then obtained, the $^{13}$C NMR and mass spectra of which oil confirm the structure as being that of 1-(2'-F-hexyl-ethanesulfoxy)-3-(2"-ethylhexyloxy)-2-propanol.

| Elemental analysis: | | | | |
|---|---|---|---|---|
| | % C | % H | % S | % F |
| Calculated | 39.20 | 4.51 | 5.51 | 42.48 |
| Measured | 38.87 | 4.60 | 5.42 | 41.96 |

Example 14

1-(2'-F-hexylethanesulfonyl)-3-(2''-ethylhexyloxy)-2-propanol 10 ml of 30% hydrogen peroxide are mixed at 25° C. with 25 ml of acetic acid and 10 drops of concentrated sulfuric acid in a 100-ml reactor.

The temperature of the mixture is brought to 10° C. A mixture of 17 g (0.3 mol) of 1-(2'-F-hexylethanethio)-3-(2''-ethylhexyloxy)-2-propanol, prepared in Example 1, and 15 ml of acetic acid is added at this temperature.

When the addition is complete, after it has returned to 25° C., the mixture is heated to 85° C. for 3 hours.

When the mixture has returned to 25° C., the solution is poured onto ice with stirring: the product is then extracted with dichloromethane. The organic phase is then washed with distilled water until the pH has returned to neutrality.

The solution is then dried over sodium sulfate and filtered through filter paper, and the solvent is thereafter evaporated off under reduced pressure. 16.2 g (90%) of a white solid are obtained, the melting point of which solid is 47° C. and the mass and $^{13}C$ NMR spectra of which solid confirm the structure as being that of 1-(2'-F-hexylethanesulfonyl)-3-(2''-ethylhexyloxy)-2-propanol.

| Elemental analysis: | | | | |
|---|---|---|---|---|
| | % C | % H | % S | % F |
| Calculated | 38.13 | 4.55 | 5.36 | 41.27 |
| Measured | 38.26 | 4.49 | 5.24 | 41.01 |

Example 15

$F-(CF_2)_{\bar{n}}-C_2H_4-S-CH_2-CHOH-CH_2-O-CH_2-CH(C_2H_5)-(CH_2)_3-CH_3$ ($\bar{n}=12$)

150 g of product consisting of a mixture of thiols of formula: $F-(CF_2)_n-C_2H_4SH$ with $n \geq 10$ and possessing an SH function value equal to 1.50 meq g$^{-1}$ (corresponding to an average value of $\bar{n}=12$), a product marketed by the company Atochem under the name "Foralkyl EM 10N®", are melted at 80° C. in a 500-ml reactor under a stream of nitrogen.

3 g of methanolic solution of sodium methylate (solution assayed at 5.65 meq g$^{-1}$) are added with stirring.

41.85 g of 2-ethylhexyl glycidyl ether are added in the course of 40 minutes at a temperature of 85° C. An orange-colored oil which solidifies at room temperature is obtained.

The product is purified by molecular distillation. 150 g of a white wax, the melting point of which ("Mettler FP 89" apparatus) is 68° C., are obtained.

Gas chromatography shows that the product consists of a mixture of products:

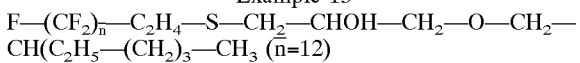

in the following proportions:

n=10:10%
n=12:53%
n=14:27.6%
n=16:8.2%
n=18:1%
n=20:0.2%

| Elemental analysis: | | | | |
|---|---|---|---|---|
| | % C | % H | % S | % F |
| Measured | 34.89 | 3.46 | 3.70 | 52.05 |

Example 16

Mixture of 1-(2'-F-octylethoxy)-2-hexanol and 2-(2'-F-octylethyloxy)-1-hexanol (49:51)

1392 g (3 mol) of 2-F-octylethanol are introduced into a 2-liter reactor. 5 ml of $BF_3/Et_2O$ are added under nitrogen and with stirring at 25° C. The mixture is brought to 80° C., and 60 g (0.6 mol) of 1,2-epoxyhexane are added dropwise while the temperature is maintained at between 80° and 85° C. When the addition is complete, the mixture is kept stirring at 80° C. for 1 hour.

After it has returned to 25° C., the mixture is washed twice with 300 ml of water which has been subjected to osmosis, once with 300 ml of water (pH 11—NaOH) and then a final time with 300 ml of water which has been subjected to osmosis.

After settling has taken place, followed by separation, the excess 2-F-octylethanol is evaporated off under reduced pressure (70° C./60 Pa). The mixture of isomers 1-(2'-F-octylethoxy)-2-hexanol and 2-(2'-F-octylethyloxy)-1-hexanol in the proportion 49:51 —assay performed by quantitative $^{13}C$ NMR—is distilled at 110° C. at 40 Pa.

236 g (70%) of a colorless viscous oil are obtained.

FORMULATION EXAMPLES

Example 1

A shampoo is prepared by mixing the following compounds:

| | |
|---|---|
| Compound of Example I | 0.2 g |
| Sodium $C_{12}$–$C_{14}$ lauryl ether sulfate (70:30) containing 2.2 mol of ethylene oxide, sold in 28% aqueous solution by the company Marchon under the name EMPICOL ESB/3FL ® | 10 g AS |
| Cocoylamidopropylbetaine/glyceryl monolaurate mixture sold in 35% aqueous solution by the company Goldschmidt under the name TEGO BETAINE HS ® | 5 g AS |
| Sodium chloride | 1 g |
| Hydroxyethylcellulose sold by the company Aqualon under the name NATROSOL 250 HHR ® | 0.5 g |
| Hydrochloric acid | qs pH 5.5 |
| Preservatives, fragrance | qs |
| Demineralized water | qs 100 g |

Hair washed with this shampoo is shiny and easy to disentangle.

The same result is obtained by replacing the compound of Preparation Example 1 in the above shampoo formulation by that of Preparation Example 10.

Example 2

An after-shampoo product is prepared by mixing the following compounds:

| | |
|---|---|
| Compound of Example 2 | 0.5 g |
| Carboxylic polymer sold by the company Goodrich under the name CARBOPOL 940 ® | 0.5 g |
| Triethanolamine      qs      pH 7 | |
| Demineralized water            qs | 100 g |

Hair treated with this after-shampoo product is sleek and shiny.

Example 3

A toothpaste is prepared by mixing the following compounds:

| | |
|---|---|
| Compound of Example 2 | 0.5 g |
| Amorphous precipitated silica sold by the company Rhone Poulenc under the name TIXOSIL 333 ® | 8 g |
| Amorphous precipitated silica sold by the company Rhone Poulenc under the name TIXOSIL 73 ® | 12 g |
| Carboxymethylcellulose sodium salt sold by the company Aqualon under the name BLANOSE 9M31F ® | 1.3 g |
| Sodium lauryl sulfate sold by the company Marchon under the name EMPICOL LXV/E ® | 1.8 g |
| Sorbitol, 70% | 30 g |
| Titanium dioxide | 1 g |
| Methyl para-hydroxybenzoate | 0.2 g |
| Sodium fluoride | 0.22 g |
| Flavoring    qs | |
| Sodium saccharinate | 0.15 g |
| Demineralized water    qs | 100 g |

Example 4

An antiperspirant stick is prepared by mixing the following compounds:

| | |
|---|---|
| Compound of Example 1 | 1.0 g |
| Stearyl alcohol | 25 g |
| Micronized anhydrous aluminum chlorohydrate | 17.5 g |
| Talc sold by the company Luzenac | 2 g |
| Butylated hydroxytoluene | 0.025 g |
| Fragrance    qs | |
| Cyclopentadimethylsiloxane/cyclotetradimethylsiloxane/cyclohexadimethylsiloxane (62 to 72:4:24) mixture sold by the company Dow Corning under the name DC 345 FLUID ® qs | 100 g |

Example 5

A foaming bath oil is prepared by mixing the following compounds:

| | |
|---|---|
| Compound of Example 2 | 2 g |
| 50:50 monoisopropanolamine lauryl ethyl sulfate/coconut acid diethanol amide mixture sold by the company Henkel under the name TEXAPON WW99 ® | 40 g |
| Sorbitan monolaurate containing 20 mol of ethylene oxide, sold by the company ICI under the name TWEEN 20 ® | 5 g |
| Virgin sesame oil | 25 g |
| Butylated hydroxytoluene | 0.1 g |
| Butylated hydroxyanisole | 0.04 g |
| Propyl para-hydroxybenzoate | 0.15 g |
| Fragrance    qs | |
| Deodorized refined rapeseed oil    qs | 100 g |

Example 6

A lipstick having the following composition is prepared:

| | |
|---|---|
| Ozokerite | 14.9 g |
| Microcrystalline wax | 4.9 g |
| Candellila wax | 7.4 g |
| Compound of Example 1 | 1.0 g |
| Jojoba oil | 6.2 g |
| Castor oil | 1.2 g |
| Lanolin | 18.6 g |
| Acetylated lanolin | 9.9 g |
| Liquid paraffin | 11.1 g |
| Talc | 3.7 g |
| Titanium mica | 8.7 g |
| D and C Red 7 calcium lake | 5.2 g |
| D and C Red 7 barium lake | 2.8 g |
| FDC Yellow 5 | 1.0 g |
| Titanium dioxide | 3.1 g |
| Butylated hydroxytoluene | 0.3 g |
| Fragrance    qs | | by mixing the oils at a temperature of 50° to 60° C. The pigments and organic lakes are ground in the oily phase.

The molten waxes, the talc and the titanium mica are then added, followed by the fragrance.

The composition is then poured into a mold.

Application of the lipstick is easy (slides readily), and the latter imparts smoothness to the lips.

Example 7

An O/W sun-protection emulsion of the following composition is prepared:

| | |
|---|---|
| Mixture of cetyl/stearyl alcohol and oxyethylenated cetyl/stearyl alcohol containing 33 mol of the ethylene oxide, sold by the company Henkel under the name SINNOWAX AO ® | 7 g |
| Non-self-emulsifying mixture of glyceryl mono- and distearates | 2 g |
| Cetyl alcohol | 1.5 g |
| Silicone oil | 1.5 g |
| Compound of Example 1 | 10 g |
| 2-Ethylhexyl para-methoxycinnamate sold by the company Givaudan under the name PARSOL MCX ® | 5 g |
| Glycerol | 15 g |
| Preservatives    qs | |
| Purified water    qs | 100 g | by first dissolving the screening agent in the fatty phase containing the emulsifiers, then heating this fatty phase to a temperature of 80° to 85° C. and adding the water, previously heated to a temperature of approximately 80° C, with brisk stirring.

The composition, which is readily applied without a sticky effect being produced, imparts smoothness to the skin while protecting it against UV radiation.

Example 8

An O/W emulsion having the following composition is prepared:

| | | |
|---|---|---|
| Capric/caprylic acid triglycerides sold by the company Dynamit Nobel under the name MIGLYOL 812 ® | | 11 g |
| Compound of Example 1 | | 5 g |
| Glycerol | | 2 g |
| Triethanolamine | | 0.80 g |
| Preservatives | qs | |
| Modified crosslinked polyacrylic acid sold by the company Goodrich under the name PEMULEN TR 2 ® | | 0.1 g |
| Crosslinked polyacrylic acid sold by the company Goodrich under the name CARBOPOL 940 ® | | 0.6 g |
| Water | qs | 100 g | by mixing; in the cold state, in the aqueous phase, the crosslinked polyacrylic acids on the one hand, and on the other hand by mixing the other ingredients which constitute the fatty phase, which is then introduced into the aqueous phase with stirring.

Example 9

An O/W emulsion is produced in the same manner as in Example 8, replacing the compound of Example 1 by the compound of Example 2.

The compositions of Examples 8 to 9, which are readily applied without a sticky effect being produced, impart smoothness to the skin.

Example 10

An aerosol hair lacquer having the following composition is prepared:

| | |
|---|---|
| Compound of Example 2 | 0.4 g |
| 90:10 vinyl acetate/crotonic acid copolymer 100% neutralized with aminomethylpropanol | 3.2 g |
| Ethanol | 33.4 g |
| Dimethyl ether | 43.0 g |
| Pentane | 20.0 g |

Hair lacquered with this composition possesses a sheen and an improved ease of brushing.

Example 11

A nail varnish having the following composition is prepared:

| | |
|---|---|
| Nitrocellulose | 10.82 g |
| Toluene-sulfonamide-formaldehyde resin sold by the company Akzo under the name KETJENFLEX MS 80 ® | 9.74 g |
| Tributyl acetylcitrate sold by the company Pfizer under the name CITROFLEX A4 ® | 6.495 g |
| Toluene | 30.91 g |
| Butyl acetate | 21.64 g |
| Ethyl acetate | 9.27 g |
| Isopropyl alcohol | 7.72 g |
| Stearalconium hectorite | 1.35 g |
| Pigments | 1.00 g |
| Citric acid | 0.055 g |
| Compound of Example 1 | 1.00 g |

The compound of Example 1 may be replaced by the compounds of Preparation Examples 8, 9 or 16.

Spreading of the varnish on the nail is easy, and a film is obtained possessing very good adhesion to the nail as well as a good sheen. Good retention of the sheen over time and good resistance of the film to abrasion are also observed.

Example 12

A shampoo of the following composition is prepared:

| | | |
|---|---|---|
| (20:40:40 $C_9/C_{10}/C_{11}$ Alkyl)poly-glycoside(1,4) sold at a concentration of 50% AS by the company Henkel under the name APG 300 ® | | 15 g AS |
| Compound of Example 1 | | 1 g |
| Fragrance, preservative | qs | |
| HCl | qs | pH 7 |
| Water | qs | 100 g |

Hair washed with this shampoo is shiny and easy to disentangle.

Example 13

A shampoo of the following composition is prepared:

| | | |
|---|---|---|
| Nonionic surfactant of the hydroxy-propyl ether type, obtained by the alkali-catalyzed condensation of 3.5 mol of glycidol with a mixture of $C_{11}$–$C_{14}$ alpha-diols according to French Patent No. 2,091,516 | | 10 g |
| Compound of Example 1 | | 0.5 g |
| Fragrance, preservative | qs | |
| natural pH = 5.8 | | |
| Water | qs | 100 g |

Hair washed with this shampoo is shiny and easy to disentangle.

Example 14
STICK FOR CARE OF THE LIPS

The following ingredients are mixed in the heated state (50°–60° C.):

| | |
|---|---|
| Carnauba wax | 10 g |
| Microcrystalline wax | 6 g |
| Castor oil | 30 g |
| Lanolin | 25 g |
| Compound of Example 1 | 2 g |
| Liquid paraffin | 12 g |
| Isopropyl lanolate | 14 g |
| Tocopherol acetate | 0.5 g |
| Vitamin A palmitate | 0.5 g |

The mixture is poured into a mold.

After cooling, a stick for care of the lips is obtained, which is easy to apply—it slides readily—and which imparts smoothness to the lips.

Example 15
MAKE-UP FOUNDATION

A make-up foundation is prepared from the following constituents:

| | |
|---|---|
| Demineralized water | 53.01 g |
| Propylene glycol | 6.5 g |
| Magnesium aluminum silicate | 1.12 g |
| Yellow iron oxide | 0.8 g |
| Brown iron oxide | 0.67 g |

| | |
|---|---|
| Black iron oxide | 0.23 g |
| Titanium oxide | 5.3 g |
| Propyl para-hydroxybenzoate | 0.05 g |
| Ethyl para-hydroxybenzoate | 0.20 g |
| Triethanolamine | 0.93 g |
| Non-self-emulsifying mixture of mono- and distearates | 0.37 g |
| Compound of Example 1 | 5 g |
| Cyclopentadimethylsiloxane | 14 g |
| Stearic acid | 1.86 g |
| Polyethylene glycol stearate containing 2 mol of ethylene oxide | 0.56 g |
| 2,4,4'-Trichloro-2'-hydroxydiphenyl ether sold by the company Ciba Geigy under the name "IRGASAN DP 300" ® | 0.1 g |
| Polyethylene powder | 9.3 g |

The water is heated to 90° C., the propylene glycol is dispersed therein and the mixture is stirred. It is cooled to 70° C. and the silicate, pigments and preservatives are added. The mixture is stirred until homogeneous. The temperature is stabilized at 60° C. and the triethanolamine is then added. The temperature is stabilized at 60° C., and the previously prepared fatty phase containing the IRGASAN DP 300® is introduced. An oil-in-water emulsion is produced by stirring. At 40° C., a polyethylene powder is added and the mixture is cooled.

Example 16

NAIL CARE SERUM

The following mixture is produced:

| | |
|---|---|
| Cyclopentadimethylsiloxane | 99.4 g |
| Tocopherol acetate | 0.1 g |
| Compound of Example 1 | 0.5 g |

This product is applied to the nail by massaging. After a sufficient time to enable the silicone to evaporate off, a varnish may be applied to the nail without its retention being impaired.

Example 17

| CREAM | |
|---|---|
| Phase A | |
| Cetyl alcohol | 4 g |
| Sorbitan tristearate | 0.9 g |
| polyethylene glycol stearate containing 40 mol of ethylene oxide | 2 g |
| Glyceryl stearate | 3 g |
| Myristyl myristate | 2 g |
| Octyl palmitate | 5 g |
| Hydrogenated polyisobutene sold by the company Nippon Oils & Fats under the name "PARLEAM" ® | 6.5 g |
| Phase B | |
| Perfluoropolyether sold by the company Ausimont under the name "FOMBLIN HCR" ® | 10.4 g |
| Compound of Example 14 | 5 g |
| Phase C | |
| Preservatives | 0.35 g |
| Glycerol | 8 g |
| Water | 16.25 g |

| CREAM | |
|---|---|
| Phase D | |
| Water | 35.3 g |
| Imidazolidinylurea | 0.3 g |

Phase A is heated to 80° C., Phase B is added thereto and the mixture is maintained at 80° C. Phase C is heated to 80° C. and added to Phases A and B. The mixture is emulsified at 80° C. and the temperature is then lowered to 45° C. Phase C is added with brisk stirring.

Example 18

CREAM

According to the same procedure as in Example 17, a cream of the following composition is prepared:

| | |
|---|---|
| Phase A | |
| Cetyl alcohol | 4 g |
| Sorbitan tristearate | 0.9 g |
| Polyethylene glycol stearate containing 40 mol of ethylene oxide | 2 g |
| Glyceryl stearate | 3 g |
| Myristyl myristate | 2 g |
| Octyl palmitate | 5 g |
| Hydrogenated polyisobutene | 6.5 g |
| Phase B | |
| Compound of Example 14 | 3 g |
| Phase C | |
| Preservatives | 0.35 g |
| Glycerol | 30 g |
| Water | 17 g |
| Phase D | |
| Imidazolidinylurea | 0.35 g |
| Water | 25.9 g |

Example 19

A lipstick having the following composition is prepared according to the same procedure as in Example 6:

| | |
|---|---|
| Ozokerite | 15 g |
| Beeswax | 8 g |
| Carnauba wax | 4 g |
| Compound of Example 12 | 2 g |
| Jojoba wax | 7 g |
| Sesame oil | 10 g |
| Castor oil | 2 g |
| Lanolin | 20 g |
| Acetylated lanolin | 10 g |
| Liquid paraffin | 10 g |
| Titanium oxide | 3 g |
| FD & C Yellow No. 6 aluminum lake | 3 g |
| DC Red No. 7 calcium lake | 6 g |
| Fragrance qs | |

Application of the lipstick is easy (slides readily), and the latter imparts smoothness to the lips.

We claim:

1. A compound of the formula

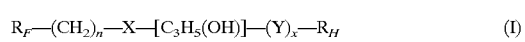

wherein $C_3H_5(OH)$ represents

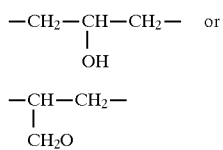

$R_F$ represents a perfluorinated $C_4$–$C_{20}$ alkyl;
$R_H$ represents a linear or branched $C_1$–$C_{22}$ alkyl, aryl or aralkyl;
n ranges from 0 to 4; and a) X represents O, x is 0 or 1, and
Y represents O, S,

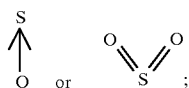

or b) X represents S,

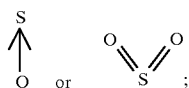

x is 1 and
Y represents O.

2. The compound of claim 1 wherein
$R_F$ represents a perfluorinated $C_6$–$C_{12}$ alkyl;
$R_H$ represents a linear or branched $C_3$–$C_{18}$ alkyl, a $C_6$–$C_{10}$ aryl or a $C_7$–$C_{15}$ aralkyl;
n=2;
X represents O or S; and
Y represents O.

* * * * *